United States Patent
Domeradzka et al.

(10) Patent No.: US 12,297,474 B2
(45) Date of Patent: May 13, 2025

(54) PROCESS TO PRODUCE MONO-RHAMNOLIPIDS

(71) Applicant: Conopco, Inc., Englewood Cliffs, NJ (US)

(72) Inventors: Natalia Eliza Iyke Domeradzka, Liverpool (GB); Dietmar Andreas Lang, Liverpool (GB); Neil James Parry, Tarporley (GB); Mark Lawrence Thompson, Ellesmere Port (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 18/286,791

(22) PCT Filed: Apr. 25, 2022

(86) PCT No.: PCT/EP2022/060823
§ 371 (c)(1),
(2) Date: Oct. 13, 2023

(87) PCT Pub. No.: WO2022/229052
PCT Pub. Date: Nov. 3, 2022

(65) Prior Publication Data
US 2024/0084353 A1     Mar. 14, 2024

(30) Foreign Application Priority Data
Apr. 29, 2021 (EP) .................... 21171230

(51) Int. Cl.
*C12P 19/44* (2006.01)
*C12N 9/24* (2006.01)
*C12N 11/00* (2006.01)

(52) U.S. Cl.
CPC ............ *C12P 19/44* (2013.01); *C12N 9/2402* (2013.01); *C12N 11/00* (2013.01); *C12Y 302/0104* (2013.01)

(58) Field of Classification Search
None
See application file for complete search history.

(56) References Cited

U.S. PATENT DOCUMENTS

| | | | |
|---|---|---|---|
| 4,971,812 | A | 11/1990 | Tsen |
| 8,658,407 | B2 | 2/2014 | Lyons et al. |
| 9,243,212 | B2 | 1/2016 | Kuppert et al. |
| 10,292,924 | B2 | 5/2019 | Schilling et al. |
| 10,941,173 | B2 | 3/2021 | Lu et al. |
| 2010/0248320 | A1 | 9/2010 | Lyons et al. |
| 2017/0175151 | A1 | 6/2017 | Ju et al. |
| 2018/0016525 | A1 | 1/2018 | Scheuermann et al. |

FOREIGN PATENT DOCUMENTS

| | | |
|---|---|---|
| CZ | 257830 B1 | 6/1988 |
| EP | 2786743 | 10/2014 |
| EP | 2787065 | 10/2014 |
| EP | 2596087 | 12/2015 |

OTHER PUBLICATIONS

Rebroš, Martin, et al. "Recombinant α-L-rhamnosidase of Aspergillus terreus immobilization in polyvinylalcohol hydrogel and its application in rutin derhamnosylation." Biocatalysis and Biotransformation 31.6 (2013): 329-334. (Year: 2013).*
Müller, Markus Michael, et al. "Rhamnolipids—next generation surfactants?." Journal of biotechnology 162.4 (2012): 366-380. (Year: 2012).*
Gerstorferová, Daniela, et al. "Recombinant α-l-rhamnosidase from Aspergillus terreus in selective trimming of rutin." Process Biochemistry 47.5 (2012): 828-835. (Year: 2012).*
Krasan, Vladimír, et al. "Immobilization of cells and enzymes to LentiKats®." Applied microbiology and biotechnology 100 (2016): 2535-2553. (Year: 2016).*
GenBank Accession No. JN899401, Aspergillus terreus alpha-L-rhamnosidase, 2012 (Year: 2012).*
Wang, Deqing, Pu Zheng, and Pengcheng Chen. "Production of a recombinant α-L-rhamnosidase from Aspergillus niger CCTCC M 2018240 in Pichia pastoris." Applied biochemistry and biotechnology 189 (2019): 1020-1037. (Year: 2019).*
Magario et al.; "Evaluation of enzyme carriers as biocatalysts for the conversion of emulsified rhamolipds"; Biocatalysis and Biotransformation; vol. 27; pp. 237-245 (2009).
Rathankumar et al.; "Application of statistical modeling for the production of highly pure rhamnolipids using magnetic biocatalysts: Evaluating its efficiency as a bioremedition agent"; Journal of Hazardous Materials; vol. 412; pp. 1-22 (2021).
Nitschke et al.; "Rhamnolipid Surfactants: An Update on the General Aspects of These Remarkable Biomolecules"; Biotechnology Progress; vol. 21; pp. 1593-1600 (2005).
Mohammad et al.; "Rhamnolipids: diversity of structures, microbial origins and roles"; Applied Microbiology and Biotechnology; vol. 86; pp. 1323-1336 (2010).
Ahmed et al.; "Methods of Enzyme Immobilzation on Various Supports"; Materials Research Foundations; vol. 44; pp. 1-28 (2019).

(Continued)

*Primary Examiner* — Robert J Yamasaki
(74) *Attorney, Agent, or Firm* — Carter, DeLuca & Farrell, LLP; George Likourezos, Esq.

(57) ABSTRACT

The invention concerns a process to convert di-rhamnolipid to mono-rhamnolipid comprising the following process steps: —(a) contact of a starting di-rhamnolipid material with an α-L-rhamnosidase enzyme which is immobilised on a support; (b) separation of the produced mono-rhamnolipid from the reaction medium and/or side products; wherein the α-L-rhamnosidase enzyme does not have β-D-glucosidase activity.

14 Claims, 4 Drawing Sheets

(56) References Cited

OTHER PUBLICATIONS

Wahab et al.; "On the taught new tricks of enzymes immobilization: An all-inclusive overview"; Reactive and Functional Polymers; vol. 152; pp. 1-26 (2020).

Gallego et al.; "Purification and Characterization of an α-L Rhamnosidase from Aspergillus terreus of interest in Winemaking"; Food Chemistry and Toxicology; vol. 66; pp. 204-209 (2001).

Magario et al.; "Kinetic Analysis and Modeling of the Liquid-Liquid Conversion of Emulsified di-Rhamnolipids by Naringinase From Penicillium decumbens"; Biotechnolgy and Bioenginereing; vol. 9999; pp. 1-11 (2008).

Puri; "Updates on naringinase: Structural and biotechnological aspects"; Applied Microbiology and Biotechnology; vol. 93; pp. 49-60 (2011).

Joanna Bodakowska-Boczniewicz, et al. "Immobilization of Naringinase from Aspergillus Niger on a Magnetic Polysaccharide Carrier," molecules dated Jun. 12, 2022, pp. 1-25, doi:10.3390/molecules25122731; 25, 2731; MDPI.

International Preliminary Report on Patentability issued in International Application No. PCT/EP2022/060823 dated Nov. 9, 2023.

International Search Report and Written Opinion issued in International Patent Application No. PCT/EP2022/060823 dated Sep. 5, 2022.

European Search Report and Written Opinion issued in European Patent Application No. EP21171230 dated Nov. 18, 2021.

International Search Report and Written Opinion issued in International Patent Application No. PCT/EP2022/060848 dated Aug. 31, 2022.

International Preliminary Report on Patentability issued in International Patent Application No. PCT/EP2022/060848 dated Nov. 9, 2023.

European Search Report and Written Opinion issued in European Patent Application No. EP21171246 dated Nov. 10, 2021.

Devries et al "Comparative genomics reveals high biological diversity and specific adaptations in the industrially and medically important fungal genus *Aspergillus*," UniProt Database Accession No. AOA1L9UF14; 2017, pp. 1-2.

\* cited by examiner

PROCESS TO PRODUCE MONO-RHAMNOLIPIDS

FIELD OF INVENTION

The present invention concerns a process to produce mono-rhamnolipids, in particular mono-rhamnolipids suitable for use in the field of detergent compositions, in particular detergent compositions for the cleaning of articles in the home and personal care fields, in particular laundry detergents and hand dish-wash detergents.

BACKGROUND OF THE INVENTION

The present invention relates to a process to produce mono-rhamnolipids.

Rhamnolipids are carboxylic acid containing anionic surfactants that consists of one or more alkyl chains connected via a beta hydroxy group to a rhamnose sugar. They may be produced by various bacterial species. Rhamnolipids are desirable as natural green surfactants, offering both sustainability benefits as well as application benefits such as good foaming profile, mildness on the skin and excellent sensorial benefits.

Di-rhamnolipids rich mixtures can be produced from fermentation processes, for example disclosed in EP 2 787 065 A1 and EP 2 786 743 A1. The di-rhamnolipids are much more easily accessible from fermentation compared to the mono-rhamnolipids. The mono-rhamnolipids are a particularly useful material in the field of detergent compositions because they produce improved cleaning in comparison to the di-rhamnolipids, see for example EP 2 596 087 A1.

One route to obtaining higher yields of mono-rhamnolipids is fermentation host strain engineering, but this is a costly and complex approach to generating mono-rhamnolipids.

Attempts have been made to enzymatically convert di-rhamnolipids to mono-rhamnolipids using an immobilised Naringinase enzyme (Margario et al, Biocatalysis and Biotransformation, July-August 2009; 27(4): 237-245). However, improvements are still desired.

There is therefore a desire to produce a simpler and cost-effective route to generate higher yields of mono-rhamnolipids.

This problem can be overcome by the process of the invention as described herein.

SUMMARY OF THE INVENTION

The invention relates to a process to convert di-rhamnolipid to mono-rhamnolipid, wherein the process comprises the following process steps:—
(a) contact of a starting di-rhamnolipid material with an α-L-rhamnosidase enzyme which is immobilised on a support;
(b) separation of the produced mono-rhamnolipid from the reaction medium and/or side products;
wherein the α-L-rhamnosidase enzyme does not have β-D-glucosidase activity.

Preferably in the process to produce mono-rhamnolipids, the α-L-rhamnosidase enzyme is from the genus *Aspergillus*, more preferably from *Aspergillus niger, Aspergillus terreus*, or *Aspergillus lentulus*, most preferably from *Aspergillus niger, Aspergillus terreus*.

Preferably in the process to produce mono-rhamnolipids, the enzyme is immobilised on a support using a technique selected from adsorption, covalent bonding, entrapment and/or crosslinking.

Preferably the starting di-rhamnolipid material has a carbon alkyl length of from $C_8$ to $C_{14}$, more preferably from $C_8$-$C_{12}$.

Preferably the resulting mono-rhamnolipid material has a carbon alkyl length of from $C_8$ to $C_{14}$, more preferably from $C_8$-$C_{12}$.

Preferably the rhamnose by-product is removed from the enzymatic reaction mixture as the reaction progresses.

Preferably in the process to produce mono-rhamnolipids, the temperature during the reaction 30 is from 10 to 60° C., preferably from 15 to 50° C., more preferably from 18 to 45° C., most preferably from 20 to 45° C.

Preferably in the process to produce mono-rhamnolipids, the pH during the reaction is from pH 5 to 10, preferably from pH 5 to 9, more preferably from pH 5.5 to 8.5, most preferably 35 from pH 6 to 8.

By using α-L-rhamnosidase enzyme that has α-L-rhamnosidase activity but also does not have β-D-glucosidase activity, the di-rhamnolipid starting material can be selectively converted to mono-rhamnolipid material. This selective nature of the process using an α-L-rhamnosidase enzyme that has α-L-rhamnosidase activity but also does not have β-D-glucosidase activity, results in the desired mono-rhamnolipid material, by selective removal of one rhamnose moiety, in contrast to other enzymes which either do not covert the di-rhamnolipid material at all, or remove both rhamnose units, neither of which results in the desired mono-rhamnolipid material.

DETAILED DESCRIPTION OF THE DRAWINGS/FIGURES

Figure 3:
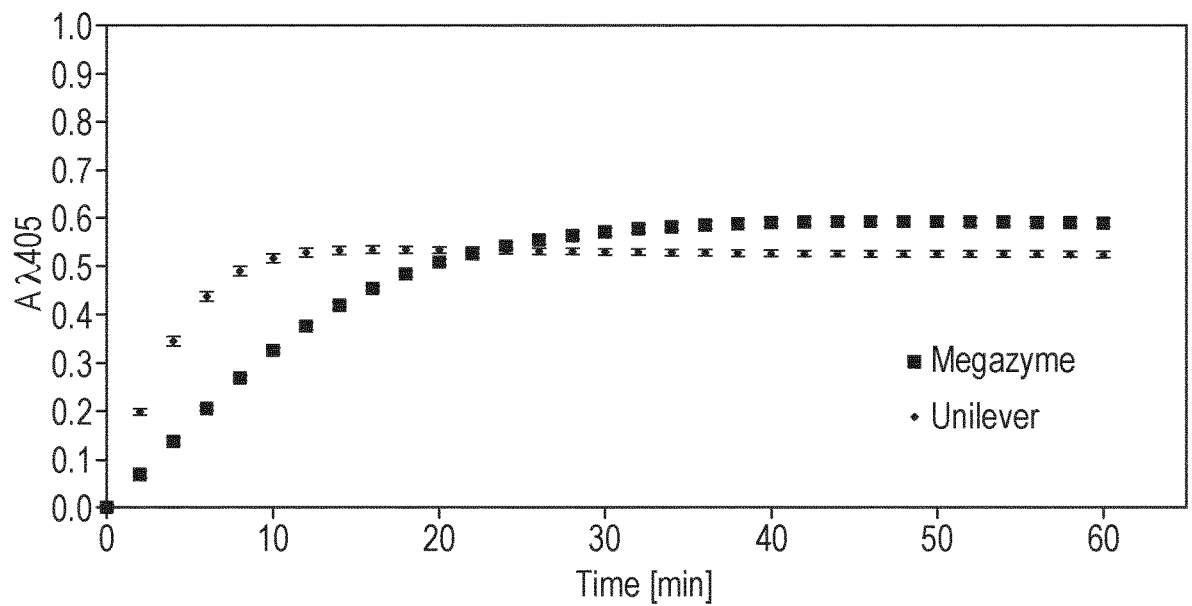

FIG. 3 shows activity assay for *A. terreus* α-L-rhamnosidase (Unilever) and *A. niger* α-L-rhamnosidase (Megazyme), using the p-nitrophenyl-α-l-rhamnopyranoside (pNPR) substrate. The enzymes facilitate the hydrolysis of pNPR into free rhamnose molecule and 4-nitrophenol (pNP). The concentration of pNP is spectrophotometrically monitored over time. The lower concentration of α-L-rhamnosidase from *A. terreus* was used to monitor kinetics due to higher activity of this enzyme. Substrate was used at 100 μM.

Figure 4:
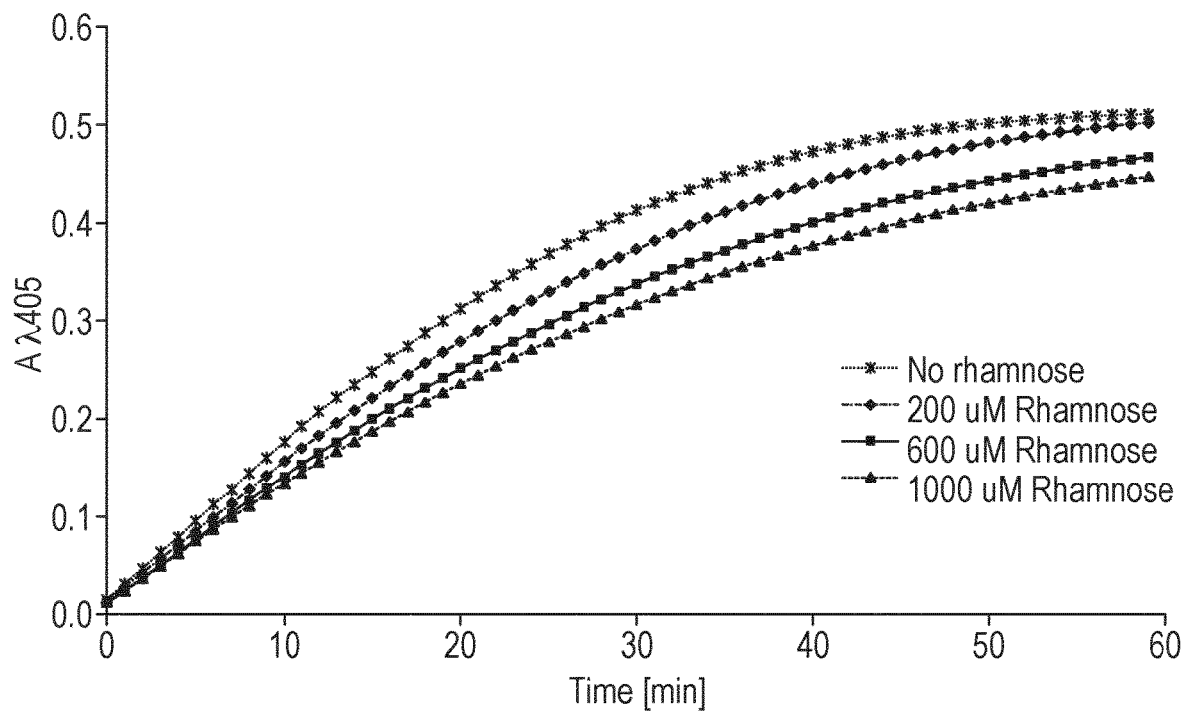

FIG. 4 shows the p-nitrophenyl-α-l-rhamnopyranoside (pNPR) based activity assay for α-L-rhamnosidase *A. terreus* (Unilever) with or without rhamnose added to reaction mixture at T0. The activity is expressed as the changes in time of the relative absorbance at 405 nm. The absorbance was measured every 30 sec. Substrate was used at 100 μM.

Figure 5:
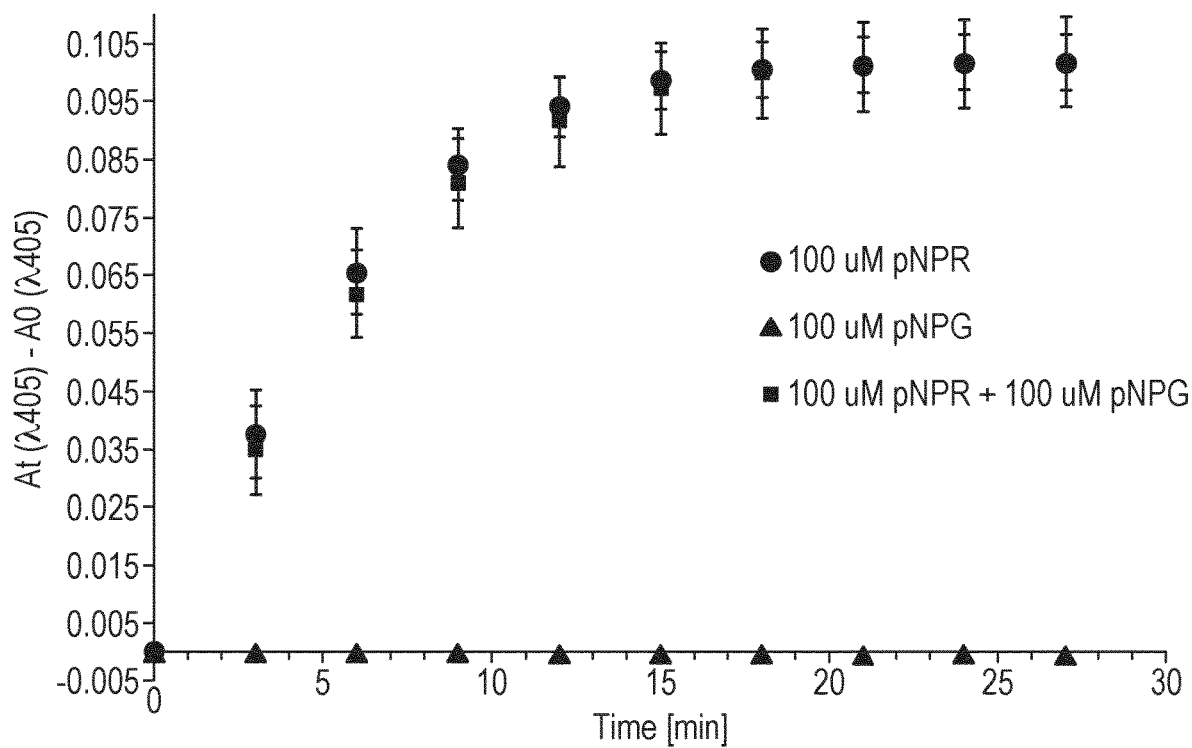

FIG. 5 shows the activity of α-L-rhamnosidase and β-D-glucosidase in enzyme from *A. terreus* was analysed using p-Nitrophenyl-α-l-rhamnopyranoside (pNPR) and p-Nitrophenyl-β-l-glucopyranoside (pNPG), respectively. The activity is expressed as the changes in time of the relative absorbance at 405 nm.

DETAILED DESCRIPTION OF THE INVENTION

The indefinite article "a" or "an" and its corresponding definite article "the" as used herein means at least one, or one or more, unless specified otherwise.

wt. % relates to the amount by weight of the ingredient based on the total weight of the composition. For anionic surfactants, wt. % is calculated based on the protonated form of the surfactant.

Rhamnolipids

Rhamnolipid is a biosurfactant. These are a class of glycolipid. They are constructed of rhamnose combined with beta-hydroxy fatty acids. Rhamnose is a sugar. Fatty acids are ubiquitous in animals and plants.

Rhamnolipids are discussed in Applied Microbiology and Biotechnology (2010) 86:1323-1336 by E. Deziel et al. Rhamnolipids are produced by Evonik, Stepan, Glycosurf, AGAE Technologies and Urumqi Unite Bio-Technology Co., Ltd. Rhamnolipids may be produced by strains of the bacteria *Pseudomonas aeruginosa*. There are two major groups of rhamnolipids; mono-rhamnolipids and di-rhamnolipids.

Mono-rhamnolipids have a single rhamnose sugar ring. A typical mono-rhamnolipid produced by *P. aeruginosa* is L-rhamnosyl-p-hydroxydecanoyl-β-hydroxydecanoate (RhaC$_{10}$C$_{10}$). It may be referred to as Rha-C$_{10}$-C$_{10}$, with a formula of C$_{26}$H$_{48}$O$_9$. Mono-rhamnolipids have a single rhamnose sugar ring.

The IUPAC Name is 3-[3-[(2R,3R,4R,5R,6S)-3,4,5-trihydroxy-6-methyloxan-2-yl]oxydecanoyloxy]decanoic acid.

Di-rhamnolipids have two rhamnose sugar rings. A typical di-rhamnolipid is L-rhamnosyl-L-rhamnosyl-p-hydroxydecanoyl-β-hydroxydecanoate (Rha2C$_{10}$C$_{10}$). It may be referred to as Rha-Rha-C-$_{10}$-C-$_{10}$, with a formula of C$_{32}$H$_{58}$O$_{13}$.

The IUPAC name is 3-[3-[4,5-dihydroxy-6-methyl-3-(3,4,5-trihydroxy-6-methyloxan-2-yl)oxyoxan-2-yl]oxydecanoyloxy]decanoic acid.

In practice a variety of other minor components with different alkyl chain length combinations, depending upon carbon source and bacterial strain, exist in combination with the above more common rhamnolipids.

Throughout this patent specification, we use the terms mono- and di-rhamnolipid in order to avoid possible confusion. However, if abbreviations are used R1 is mono-rhamnolipid and R2 is di-rhamnolipid.

Suitable Di-Rhamnolipid Starting Materials

Preferably the rhamnolipid is a di-rhamnolipid of formula: Rha2C$_{8-14}$C$_{8-14}$. The preferred alkyl chain length is from C$_8$ to C$_{12}$. The alkyl chain may be saturated or unsaturated.

The following rhamnolipids have been detected as produced by the following bacteria:

(C12:1, C14:1 indicates fatty acyl chains with double bonds).

Rhamnolipids produced by *P. aeruginosa* (di-rhamnolipids):

Rha-Rha-C8-C10, Rha-Rha-C8-C12:1, Rha-Rha-C10-C8, Rha-Rha-C10-C10, Rha-Rha-C10-C12:1, Rha-Rha-C-10-C-12, Rha-Rha-C-12-C-10, Rha-Rha-C-12:1-C-12, Rha-Rha-C-10-C14:1.

Rhamnolipids produced by *Burkholderia pseudomallei* (di-rhamnolipids):

Rha-Rha-C14-C14.

Rhamnolipids produced by *Burkholderia (Pseudomonas) plantarii* (di-rhamnolipids):

Rha-Rha-C14-C14.

A typical di-rhamnolipid is L-rhamnosyl-L-rhamnosyl-p-hydroxydecanoyl-β-hydroxydecanoate (Rha$_2$C$_{10}$C$_{10}$ with a formula of C$_{32}$H$_{58}$O$_{13}$).

Preferably the starting di-rhamnolipid material has a carbon alkyl length of from C$_8$ to C$_{14}$, more preferably from C$_8$-C$_{12}$.

Preferred Mono-Rhamnolipid Products

Preferably the resulting mono-rhamnolipid is a mono-rhamnolipid of formula: RhaC$_{8-14}$C$_{8-14}$. The preferred alkyl chain length is from C$_8$ to C$_{12}$. The alkyl chain may be saturated or unsaturated.

A preferred mono-rhamnolipid material is L-rhamnosyl-β-hydroxydecanoyl-β-hydroxydecanoate (RhaC$_{10}$C$_{10}$ with a formula of C$_{26}$H$_{48}$O$_9$).

Preferably the resulting mono-rhamnolipid material has a carbon alkyl length of from C$_8$ to C$_{14}$, more preferably from C$_8$-C$_{12}$.

α-L-Rhamnosidase Enzyme

By using α-L-rhamnosidase enzyme that has α-L-rhamnosidase activity but also does not have β-D-glucosidase activity, the di-rhamnolipid starting material can be selectively converted to mono-rhamnolipid material. This selective nature of the process using an α-L-rhamnosidase enzyme that has α-L-rhamnosidase activity but also does not have β-D-glucosidase activity, results in the desired mono-rhamnolipid material, by selective removal of one rhamnose moiety, in contrast to other enzymes which either do not convert the di-rhamnolipid material at all, or remove both rhamnose units, neither of which results in the desired mono-rhamnolipid material.

The α-L-rhamnosidase enzyme is preferably from the genus *Aspergillus*.

Preferably the α-L-rhamnosidase enzyme is from *Aspergillus niger*, *Aspergillus terreus*, or *Aspergillus lentulus*. More preferably the α-L-rhamnosidase enzyme is from *Aspergillus niger*, or *Aspergillus terreus*.

In the process of the invention, the enzyme may suitably be immobilised.

Process Details

The invention relates to a process to convert di-rhamnolipid to mono-rhamnolipid comprising the following process steps:—

(a) contact of a starting di-rhamnolipid material with an α-L-rhamnosidase enzyme which is immobilised on a support;

(b) separation of the produced mono-rhamnolipid from the reaction medium and/or side products;

wherein the α-L-rhamnosidase enzyme does not have β-D-glucosidase activity.

Preferably the rhamnose by-product is removed from the enzymatic reaction mixture as the reaction progresses. This can result in higher conversion and/or yield or the mono-rhamnolipid product.

Preferably in the process to produce mono-rhamnolipids, the temperature during the reaction is from 10 to 60° C., preferably from 15 to 50° C., more preferably from 18 to 45° C., most preferably from 20 to 45° C.

Preferably in the process to produce mono-rhamnolipids, the pH during the reaction is from pH 5 to 10, preferably from pH 5 to 9, more preferably from pH 5.5 to 8.5, most preferably from pH 6 to 8.

Immobilisation of Enzymes

The α-L-rhamnosidase enzyme can potentially be immobilised to improve characteristics such as activity, selectivity and specificity, as well as enzyme stability. The immobilisation itself can be performed by a physical interaction between enzyme and matrix or through a chemical process such as covalent bond formation between the enzyme and support. The typical lab procedure may involve, but not be limited to adsorption, covalent bonding, entrapment, and crosslinking. These methods are described in more detail in Materials Research Foundations (2019) 44:1-28 by M. Javed et al. as well as in Reactive and Functional Polymers (2020) 152: 104613 by R. Wahab et al.

Preferably in the process to produce mono-rhamnolipids, the enzyme is immobilised on a support using a technique selected from adsorption, covalent bonding, entrapment and/or crosslinking.

Preferred commercial enzyme immobilisation materials include Praesto™ and Lifetech™ available from Purolite.

The invention will be further described with the following non-limiting examples.

EXAMPLES

Experimental Methods and Materials
Enzymes and Chemicals

Three enzyme variants with α-L-rhamnosidase activity were considered in this study:
  (i) α-L-rhamnosidase from *Aspergillus niger* was obtained from Megazyme LTD (Bray, Ireland),
  (ii) recombinant α-L-rhamnosidase from *Aspergillus terreus* was prepared internally, following biosynthetic methodology as described by Weignerove et al. 2012 (43), and (iii) naringinase (sample outsourced, source and origin unknown).

Megazyme enzyme from *A. niger* was supplied as an ammonium sulphate suspension in 0.02% (w/v) sodium azide. *A. terreus* rhamnosidase, secreted in *P. pastoris*, was supplied in form of supernatant at total protein concentration of 1.7 mg/mL, and the sample for analysis was purified on the nickel column using 50 mM sodium phosphate elution buffer containing 500 mM of imidazole, Sigma Aldrich (Gillingham, United Kingdom) at pH 6.5, and dialysed against the same buffer without imidazole.

Rhamnolipid sample used in this study was obtained from Evonik (Witten, Germany), in form of 50% (w/v) water solution. The sample is a blend consisting of the various rhamnolipid congeners, with the major congener, (Rha-Rha-C10-C10), 2-O-alpha-L-rhamnosyl-alpha-L-rhamnosyl-3-hydroxydecanoyl-3-hydroxydecanoic acid and it will be referred hereafter as RL2. This sample also contains a minor amount of rhamnosyl-3-hydroxydecanoyl-3-hydroxydecanoate congener (Rha-C10:0/C10:0), which will be referred hereafter as RL1. The expected molecular weight of RL1 is 504.321 g*mol-1, and the expected molecular weight of RL2 is 649.378 g*mol-1.

All other chemicals were obtained from Sigma Aldrich (Gillingham, United Kingdom) unless otherwise stated in the methods below.
HPLC-CAD Instrumentation and Method Parameters for Rhamnolipid Analysis RL2 samples were diluted in acetonitrile to final concentration of 0.75 mM, filtered with 0.45 μm nitrocellulose syringe filter, and applied onto column for analysis. The fractions were collected in 30 sec rate per fraction and subjected to MALDI-TOF analysis. Next, RL2 were used as substrates for enzymes from *A. terreus* and *A. niger*, and naringinase.

For each reaction, the enzymes were used in concentration 1.2 mg*mL- and substrate was used at 1 mM. Both reactions were performed in 50 mM MES buffer, pH 6.5. The total volume of the reaction mix was 1 mL. Both samples were incubated at 40° C. and 225 rpm for 24 hours in incubator shaker (Infors HT, Surrey). 100 μL of reaction mixture was diluted in acetonitrile at ratio 1:10, filtered with 0.45 μm nitrocellulose syringe filter, and applied onto the C18 column. The control sample (i.e. R2 benchmark) was not treated with any enzyme.

Rhamnolipid analysis was carried out using a Dionex UltiMate 3000 system (Thermo Scientific, Dreieich, Germany) composed of an RS Dual Gradient pump, an RS Autosampler, an RS Column Compartment, an RS Diode Array Detector and a Corona Veo SD Charged-Aerosol Detector (CAD). The response in this type of detector is proportional to mass of analyte reaching the detector per unit time and it is expressed in picoampere (pA).

Chromatographic separation was performed using Accucore™ C18 LC Column (150×4.6 mm, 2.6 μm) (Thermo Scientific, Dreieich, Germany) at ambient temperature. The flow rate was set to 1 mL/min. Mobile phase gradient consisting of 0.02% acetic acid/water (v/v) (A) and 100% acetonitrile (B) was used. The gradient was set to 70% B from 0 to 2 min, increased to 82% B from 2 to 4 min, remained constant for 1 min, and increased to 88% B from 5 to 8 min before it immediately decreased to 70% and remained constant for equilibration. Total run time was 12 min. The injection volume was 10 μL. Charged-aerosol detection was performed at ambient temperature with an acquisition rate of 10 Hz and a filter constant of 3.6. CAD nitrogen gas pressure was 35 psi. Chromeleon V7.2 software was used for general HPLC-control, data acquisition and analysis for CAD measurements.
Analysis of RLs by Matrix-Assisted Laser Desorptionionization Time of Flight Mass Spectrometry (MALDI TOF MS)

MALDI-TOF was used for analysis RL2 fractions collected as described above. The matrix solution was 2,5-dihydroxybenzoic acid dissolved in 50% aqueous acetonitrile containing 0.1% trifluoroacetic acid (TFA). 1 μL of HPLC fractionations, 1 μL of matrix solution and 2 μL of distilled water were mixed in an Eppendorf tube. 1 μL of the matrix-sample mixture was spotted onto the stainless-steel anchor chip. The spots were air-dried at room temperature and then analysed by MALDI TOF MS, using UltraflexIII MALDI-TOF/TOF mass spectrometer (Bruker, Billerica, MA) operated with Smart beam laser system.

Figure 1:
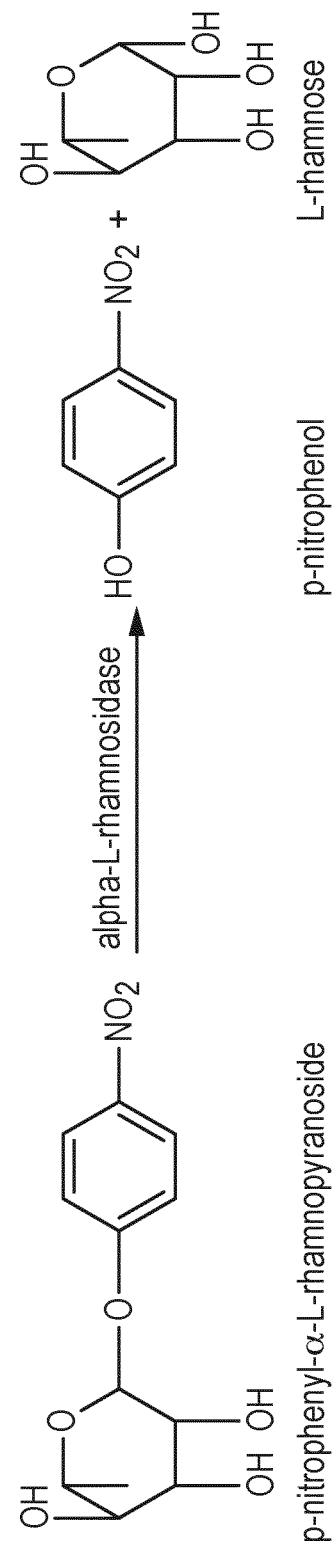
FIG. 1 shows that in the rhamnosidase activity assay the amount of p-nitrophenol released by α-L-rhamnosidase can be obtained by colorimetric measurement at 405 nm.

The rhamnolipid MS spectra were attained in a positive mode reflector; the used parameters for RLs detection were: ion source 1, 25.08 kV and 2, 21.72 kV; reflector, 26.42 kV and 13.867 kV; lens, 9.28 kV. The LIFT mode was applied for MS/MS analysis, using the following considerations: ion source 1, 8.01 kV and 2, 7.21 kV; reflector, 29.50 kV and 2, 13.91 kV; lens, 3.61 kV; LIFT 1, 19.08 kV and LIFT 2, 2.71 kV. The used mass range for measurements was m/z 300-4000 Da and a maximum MS deviation of 0.5 Da. 4000 laser shots were accumulated with increments of 200 shot, to represent the final mass spectrum. External MS calibration was conducted using peptide calibration standard II (Bruker Daltonics), FlexControl V. 3.4 software was used for system control, where FlexAnalysis V. 3.4 and BioTools V. 3.2 software were used for data processing.
Rhamnosidase Activity Assessment α-l-Rhamnosidase activity of enzyme from *A. terreus* and enzyme from *A. niger* was determined by a colorimetric method using p-nitrophenyl-α-l-rhamnopyranoside (pNPR) (See the chemical formula equation shown in FIG. 1). The pNPR substrate was first dissolved in DMSO, with concentration adjusted to 200 μM in 100 mM sodium phosphate buffer pH 6.5. Enzymes were diluted to concentration of 20 μg/mL in 100 mM sodium phosphate buffer pH 6.5. The reaction was prepared by mixing the substrate solution with enzyme solution in 1:1 ratio. The activity assay was performed on 96-well Microtiter UV plate by Thermo Scientific (Waltham, MA USA). All reactions were done at pH 6.5 and in temperature 40° C. The changes in absorbance were monitored at 405 nm for 60 minutes in Microplate reader Varioskan® Flash.

Influence of pH and Temperature on Rhamnosidase Activity

The analysis was performed only for α-l-rhamnosidase from *A. terreus*. The influence of temperature change and pH change on enzyme activity was investigated using the same colorimetric method as described above (See FIG. 1). The pNPR substrate was first dissolved in DMSO, with concentration adjusted to 200 μM in a buffer of choice. Enzyme was diluted to concentration of 20 μg/mL in a buffer of choice. The reaction was prepared by mixing the substrate solution with enzyme solution in 1:1 ratio. The activity assay was performed on 96-well Microtiter UV plate by Thermo Scientific (Waltham, MA USA). For analysis of the pH influence on enzyme activity, the reactions were performed in 40° C., and buffers of choice were: 100 mM sodium phosphate buffer pH 6.5, 100 mM Tris-HCl buffer pH 7.5, 100 mM Tris-HCl buffer pH 8.5, and 100 mM sodium carbonate buffer pH 10.5. For analysis of the temperature influence on enzyme activity, the reactions were performed in 20° C. and 40° C., in 100 mM sodium phosphate buffer at pH 6.5. The changes in absorbance were monitored at 405 nm for 30 minutes in Microplate reader Varioskan® Flash. The standard curve for the p-nitrophenol (pNP) release was prepared by measurement of absorbance at 405 nm for series of pNP samples of different concentrations (in 100 mM of corresponding buffer).

Influence of Rhamnose Excess on Rhamnosidase Activity

The analysis was performed only for α-l-rhamnosidase from *A. terreus*. The influence of rhamnose excess on enzyme activity was investigated using the same colorimetric method as described above (See FIG. 1). The pNPR substrate was first dissolved in DMSO, with concentration adjusted to 300 μM in 100 mM sodium phosphate buffer pH 6.5. Enzymes were diluted to concentration of 30 μg/mL in 100 mM sodium phosphate buffer pH 6.5. Following sequence of rhamnose concentrations were prepared in 100 mM sodium phosphate buffer pH 6.5:0.6 mM, 1.2 mM, 1.8 mM, 2.4 mM, 3 mM. 240 μL of the total reaction mixture was prepared by adding the substrate solution, the enzyme solution and the rhamnose solution in 1:1:1 ratio. The activity assay was performed on 96-well Microtiter UV plate by Thermo Scientific (Waltham, MA USA). All reactions were done at pH 6.5 and in temperature 40° C. The changes in absorbance were monitored at 405 nm for 30 minutes in Microplate reader Varioskan® Flash.

β-D-Glucosidase Activity Assessment

β-D-glucosidase activity of enzyme from *A. terreus* was determined by a colorimetric method using p-nitrophenyl-β-l-glucopyranoside (pNPG). The pNPG substrate was first dissolved in DMSO, with concentration adjusted to 200 μM in 100 mM sodium phosphate buffer pH 6.5. To analyse the substrate preference, the pNPG was mixed with pNPR at 1:1 ratio, then dissolved in DMSO, and concentration of such mixture was adjusted to 200 μM in 100 mM sodium phosphate buffer pH 6.5. As a control, pNPR, prepared as above, at concentration of 200 μM was used. Enzyme was diluted to concentration of 20 μg/mL in 100 mM sodium phosphate buffer pH 6.5. The reactions were prepared by mixing the substrate solution with enzyme solution in 1:1 ratio. The activity assay was performed on 96-well Microtiter UV plate by Thermo Scientific (Waltham, MA USA). All reactions were done at pH 6.5 and in temperature 40° C. The changes in relative absorbance values were monitored at 405 nm for about 30 minutes in Microplate reader Varioskan® Flash.

Example 1—RP-HPLC Analysis of Enzymatically Treated Di-Rhamnolipids

We evaluated the ability of utilizing rhamnolipids as substrates by α-L-rhamnosidase using *A. terreus* α-L-rhamnosidase, *A. niger* α-L-rhamnosidase and naringinase.

The substrate sample was mixed with the studied enzyme at a concentration of 1 mg/mL and reactions were performed at 40° C., in pH 6.5 for 24 hours. For the control, R2 sample was mixed with buffer only. Next, the reactions were analysed using RP-HPLC, and the control was additionally analysed using MAL-TOF, to confirm which peak corresponds to R1 and R2 congeners.

Figure 2:
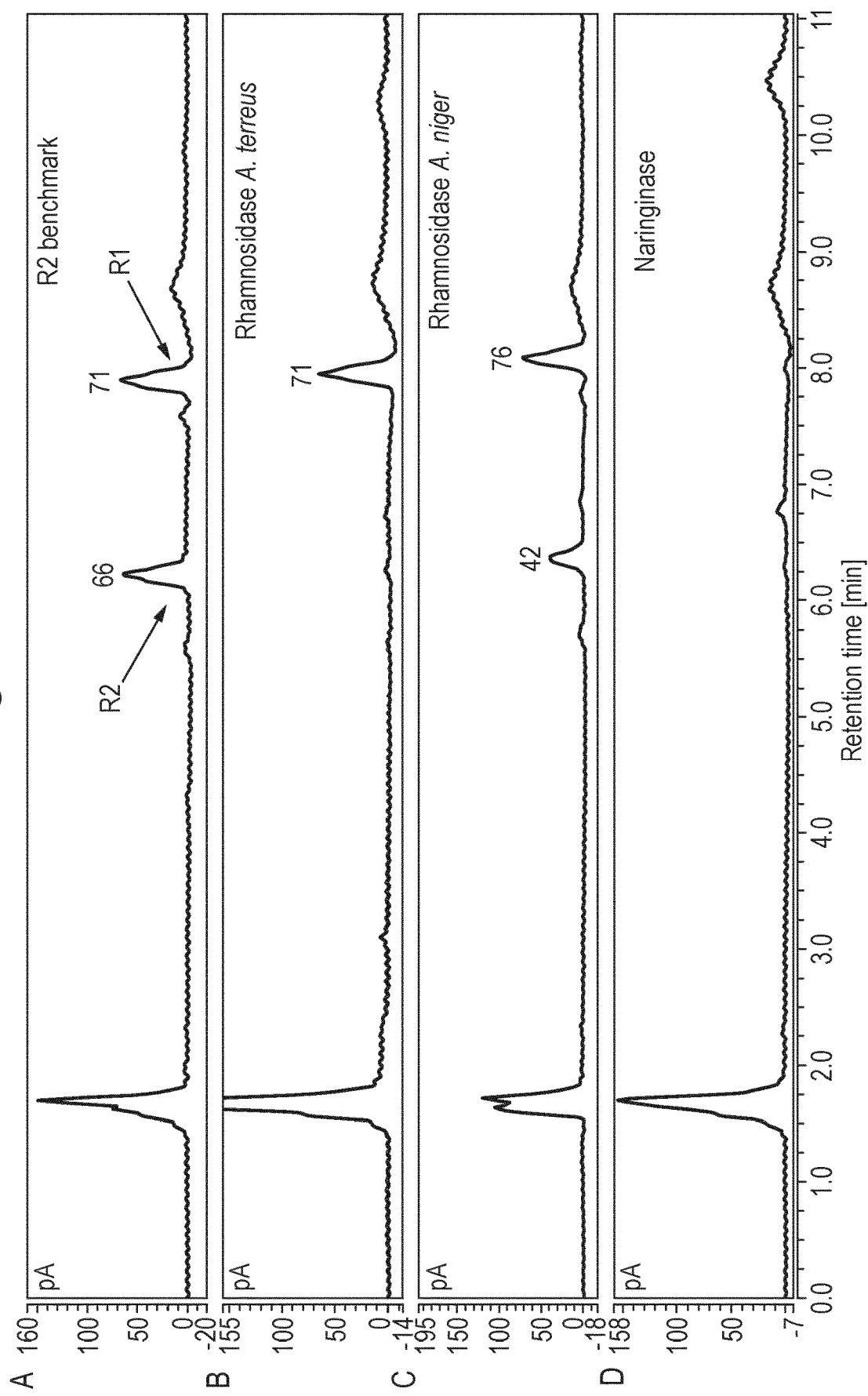
FIG. 2 shows a comparison of RP-HPLC chromatograms for di-rhamnolipid (RL2) sample: (A) untreated, (B) treated with rhamnosidase originated from *A. terreus*, (C) treated with rhamnosidase originated from *A. niger*, and (D) treated with commercial naringinase.

In FIG. 2, the peak detected between 1 and 2 min of retention time corresponds to void. The peak detected at 6.5 min of the retention time corresponds to di-rhamnolipid fraction of the sample and the peak detected at 8.2 min of the retention time corresponds to the more hydrophobic mono-rhamnolipid fraction. The fractions were collected, and their molecular masses were analysed by MALDI-TOF.

The chromatogram of the control sample presented two peaks at 6.5 min of retention time and 8.2 min of retention time (see FIG. 2, A). The MALDI-TOF analysis revealed that MW of the substance eluted after 6.5 min was corresponding to that of estimated MW for R2 and that MW of the substance eluted after 8.2 min was corresponding to that of estimated MW for R1 (data not included). The analysis of the samples after 24 h of enzymatic treatment revealed changes in the chromatogram for each reaction.

The chromatogram of the sample treated by enzyme from *A. terreus* revealed that only R1 peak was detected (see FIG. 2, B). In the sample treated by enzyme from *A. niger*, both R2 and R1 peak were detected on chromatogram, however, peak R2 was much smaller in comparison to the control (see FIG. 2, C). In sample treated by naringinase, none of these peaks were detected (see FIG. 2, D). This suggests that naringinase, possesses both α-l-rhamnosidase and β-d-glucosidase activities, and fully trims rhamnose from rhamnolipid molecule. Due to this character of naringinase, the enzyme cannot be utilized for production of mono-rhamnolipids and it will be not further assessed.

Example 2—Activity of α-L-Rhamnosidase Enzymes of Different Origin

The relative activity of α-L-rhamnosidase from *A. terreus* and α-L-rhamnosidase from *A. niger* were measured against the p-NPR. The reaction was monitored in time at 40° C. and pH 6.5 (See FIG. 3). The enzymes caused release of the product—4-nitrophenol. Both enzymes showed different kinetic behaviour, with *A. terreus* enzyme acting faster, however, reaching plateau after 10 min at 70% of converted substrate. *A. niger* enzyme converted similar amount of substrate after 30 min., however, after that, the conversion did not reach plateau and this enzyme converted 10% more substrate than *A. terreus* after 60 min, with the kinetic curve suggesting that with longer time of reaction, the substrate could be fully converted. The 70% conversion of R2 is plenty sufficient for test purposes, therefore the enzyme with faster kinetics was used for further analysis.

Example 3—Influence of Rhamnose on Rhamnosidase Activity

The relative activity of α-L-rhamnosidase from *A. terreus* was measured using pNPR substrate in the excess of rhamnose in the reaction mix. The analysis was performed in order to study product inhibition phenomenon. The monitoring of the enzyme activity in the reactions with various rhamnose concentrations has showed that the substrate conversion rate decreased in the reactions with increasing amount of rhamnose added (See FIG. 4). This result suggests that the rhamnose generated during the reaction time might cause enzyme inhibition, which in turn hampers the full substrate conversion, so that selective removal of the rhamnose from the reaction medium will enable improved conversion to the desired mono-rhamnolipid material.

Example 4—β-D-Glucosidase Activity Assessment pNPG was used as a substrate to monitor β-D-glucosidase activity of enzyme from *A. terreus*, the pNPR was used as a substrate showing α-l-rhamnopyranoside activity, and mixture of both substrates was used to determine substate preference (see FIG. 5). The analysis has shown that enzyme from *A. terreus* recognized only pNPR as a substrate. The absorbance signal was not detected for the reaction with pNPG, and the reaction kinetics observed for pNPR substrate was not impacted by presence of pNPG in the reaction with mixed substrates. This result shows that enzyme from *A. terreus* do not possesses β-D-glucosidase activity.

The invention claimed is:

1. A process to convert di-rhamnolipid to mono-rhamnolipid comprising the following process steps:
  (a) contacting a starting di-rhamnolipid material with an α-L-rhamnosidase enzyme which is immobilised on a support;
  (b) separating a produced mono-rhamnolipid from a reaction medium and/or side products;
  wherein the α-L-rhamnosidase enzyme does not have β-D-glucosidase activity and is from *Aspergillus lentulus*, and the resulting mono-rhamnolipid material has a carbon alkyl length of from $C_8$ to $C_{14}$.

2. The process according to claim 1, wherein the enzyme is immobilised on a support using a technique selected from adsorption, covalent bonding, entrapment, crosslinking, and any combination thereof.

3. The process according to claim 1, wherein the starting di-rhamnolipid material has a carbon alkyl length of from $C_8$ to $C_{14}$.

4. The process according to claim 3, wherein the starting di-rhamnolipid material has a carbon alkyl length of from $C_8$-$C_{12}$.

5. The process according to claim 1, wherein a rhamnose by-product is removed from the enzymatic reaction mixture as the reaction progresses.

6. The process according to claim 1, wherein a temperature during the reaction is from 10 to 60° C.

7. The process according to claim 6, wherein the temperature during the reaction is from 15 to 50° C.

8. The process according to claim 6, wherein the temperature during the reaction is from 18 to 45° C.

9. The process according to claim 6, wherein the temperature during the reaction is from 20 to 45° C.

10. The process according to claim 1, wherein a pH during the reaction is from pH 5 to 10.

11. The process according to claim 10, wherein the pH during the reaction is from pH 5 to 9.

12. The process according to claim 10, wherein the pH during the reaction is from pH 5.5 to 8.5.

13. The process according to claim 10, wherein the pH during the reaction is from pH 6 to 8.

14. The process according to claim 1, wherein the resulting mono-rhamnolipid material has a carbon alkyl length of from $C_8$-$C_{12}$.

* * * * *